United States Patent
Kleina et al.

(10) Patent No.: US 6,369,104 B1
(45) Date of Patent: Apr. 9, 2002

(54) BIOCIDAL COMPOSITIONS AND USE THEREOF CONTAINING A SYNERGISTIC MIXTURE OF GLUTARALDEHYDE AND 2,2-DIBROMO-3 NITRILO PROPIONAMIDE

(75) Inventors: Lynn G. Kleina, Perkasie; Wilson K. Whitekettle, Jamison, both of PA (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/617,417

(22) Filed: Jul. 17, 2000

(51) Int. Cl.[7] ................. A01N 37/34; A01N 35/00
(52) U.S. Cl. ................. 514/528; 514/705
(58) Field of Search .................. 514/705, 528

(56) References Cited

U.S. PATENT DOCUMENTS

| | | | |
|---|---|---|---|
| 4,732,913 A | 3/1988 | Donofrio et al. | 514/528 |
| 4,916,159 A | 4/1990 | Whitekettle et al. | 514/528 |
| 5,008,023 A | 4/1991 | Conlan et al. | 210/764 |
| 5,039,708 A | 8/1991 | Conlan et al. | 514/705 |
| 5,041,463 A | 8/1991 | Whitekettle et al. | 514/634 |
| 5,063,248 A | 11/1991 | Conlan et al. | 514/665 |
| 5,134,160 A | 7/1992 | Whitekettle et al. | 514/479 |
| 5,158,972 A | 10/1992 | Whitekettle et al. | 514/471 |

OTHER PUBLICATIONS

Kelley, M. T. and Matsen, J. M., *Antimicrobial Agents and Chemeotherapy*, 9:440 (1976).
Kull, F. C., Eisman, P.C., Sylwestrowicz, H. D., and Mayer, R. L., *Applied Microbilogy*, 9,538 (1961).
21 US. Code of Federal Regulations Section 1 76.300 (1999).

*Primary Examiner*—Allen Robinson
(74) *Attorney, Agent, or Firm*—Mark A. Hagedorn; Steven D. Boyd

(57) ABSTRACT

A microbial inhibiting composition and method are disclosed. The composition comprises an amount, effective for the intended purpose, of glutaraldehyde and 2,2-dibromo-3-nitrilopropionamide. The method comprises administering between about 0.1 and 200 parts of this combined treatment (based on one million parts of the desired aqueous system) to the particular water containing system for which treatment is desired.

16 Claims, No Drawings

BIOCIDAL COMPOSITIONS AND USE THEREOF CONTAINING A SYNERGISTIC MIXTURE OF GLUTARALDEHYDE AND 2,2-DIBROMO-3 NITRILO PROPIONAMIDE

BACKGROUND OF THE INVENTION

The formation of slimes by microorganisms is a problem that is encountered in many aqueous systems. For example, the problem is not only found in natural waters such as lagoons, lakes, ponds, etc., and confined waters as in pools, but also in such industrial systems as cooling water systems, air washer systems, secondary/tertiary oil production operations, and pulp and paper mill systems. All possess conditions which are conducive to the growth and reproduction of slime-forming organisms. In both once-through and recirculating cooling systems, for example, which employ large quantities of water as a cooling medium, the formation of slime by microorganisms is an extensive and constant problem. Furthermore, the slime can also support the growth of other microbes as part of the environment. The possibility exists that some of these organisms are pathogens such as *Legionella pneumophila*.

Airborne organisms are readily entrained in the water from cooling towers and find this warm medium an ideal environment for growth and replication. Aerobic and heliotropic organisms flourish on the tower deck and other tower surfaces proper, whereas others circulate in the bulk water throughout the system, attach and grow in areas such as the sump, piping, and passages of the cooling system. The slime formation not only aids in the deterioration of the tower structure, but also, acts as the source of microbes that can break off, deposit on metal surfaces, and form biofilms promoting corrosion. Slime carried through the cooling system plugs and fouls lines, valves, strainers, etc. and deposits on heat exchange surfaces. In the latter case, the impedance of the heat transfer can greatly reduce the efficiency of the cooling system.

In pulp and paper mill systems, slime formed by microorganisms is commonly encountered and causes fouling, plugging, or corrosion of the system. The slime also becomes entrained in the paper produced to cause breakouts on the paper machines, which results in work stoppages and the loss of production time. The slime is also responsible for unsightly blemishes in the final product, which result in rejects and wasted output.

In secondary/tertiary oil recovery operations where water flooding is employed, slime forming microbes on pipe surfaces can host the attachment and protection of other organisms such as sulfate reducers and other anaerobes causing corrosion resulting in degradation and leaks of pipelines.

The previously discussed problems have resulted in the extensive utilization of biocides in cooling water and pulp and paper mill systems. Materials which have enjoyed widespread use in such applications include chlorine, chlorinated phenols, bromine compounds, organo-bromines, and various organo-sulfur compounds. All of these compounds are generally useful for this purpose especially against bacterial microorganisms, but each is attended by a variety of impediments. For example, chlorination is limited both by its specific toxicity for slime forming organisms at economic levels and by the tendency of chlorine to react non-specifically with organic material resulting in the expenditure of the chlorine before its full biocidal function is achieved. Often the thickness of a well-established slime biofilm inhibits chlorine from penetrating the biofilm, so only the surface organisms are destroyed, allowing for quick recovery and growth. The sulfate reducing bacteria are not affected and the corrosion rates will continue. Other biocides are attended by odor problems and hazards in respect to storage, use, or handling which limit their utility. To date, no one compound or type of compound has achieved a clearly established predominance with respect to the applications discussed. Likewise, lagoons, ponds, lakes, and even pools, either used for pleasure purposes or used for industrial purposes for disposal and storage of industrial wastes, become, during the warm weather, besieged by slime due to microorganism growth and reproduction. In the case of the recreational areas, the problem of infection is obvious. In the case of storage or disposal of industrial materials, the microorganisms cause additional problems which must be eliminated prior to the material'ss use or disposal of the waste.

Naturally, economy is a major consideration with respect to all of these biocides. Such economic considerations are attached to both the cost of the biocide and the expense of its application. The cost performance index of any biocide is derived from the basic cost of the material, its effectiveness per unit weight, the duration of its biocidal or biostatic effect on the system treated, and the ease and frequency of its addition to the system treated. To date, none of the commercially available biocides has exhibited a prolonged biocidal effect. Instead, their effectiveness is rapidly reduced as the result of exposure to physical conditions such as temperature, association with ingredients contained by the system toward which they exhibit an affinity or substantivity, pH, etc., with a resultant restriction or elimination of their biocidal effectiveness, or by dilution.

As a consequence, the use of such biocides involves their continuous or frequent addition to systems to be treated and their addition to multiple points or zones in the systems to be treated. Accordingly, the cost of the biocide and the labor costs associated with such means of applying it are considerable. In other instances, the difficulty of access to a zone or entire zone in which slime formation is experienced precludes the effective use of a biocide. For example, if in a particular system there is no access to an area at which slime formation occurs such as tower fill, the biocide can only be applied at a point which is upstream in the flow system. The physical or chemical conditions, e.g., chemical reactivity, thermal degradation, etc., which exists between the point where the biocide may be added to the system and the point at which its biocidal effect is desired, sometimes render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at multiple points, and even then a diminishing biocidal effect will be experienced between one point of addition to the system and the next point downstream at which the biocides may be added. In addition to the increased cost of utilizing and maintaining multiple feed points, gross ineconomies with respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

SUMMARY OF THE INVENTION

The biocidal compositions of the present invention comprise, as active ingredients, 1) glutaraldehyde and 2)

2,2-dibromo-3-nitrilopropionamide (DBNPA). These constituents are commercially available. The synergistic effect obtained by combining glutaraldehyde and DBNPA has not been previously disclosed.

DETAILED DESCRIPTION OF THE INVENTION

Surprisingly, the present inventors have found that mixtures of glutaraldehyde and DBNPA are especially efficacious in controlling the growth of bacterial microbes, specifically the *Klebsiella pneumoniae* species. This particular species is a member of the capsulated, facultative class of bacteria and is generally present in water, air, and soil. These bacteria continually contaminate open cooling systems and pulping and papermaking systems and are among the most common slime formers. The slime may be viewed as being a mass of agglomerated cells stuck together by the cementing action of the gelatinous polysaccharide or proteinaceous secretions around each cell. The slimy mass entraps other debris, restricts water flow and heat transfer, may serve as a site for corrosion, and helps form an excellent habitat for bacterial, fungal, and protozoan species, amongst which may be pathogens, e.g., Legionella.

The fact that the Klebsiella specie used in the tests is a facultative species is important as, by definition, such bacteria may thrive under aerobic or anaerobic conditions. Accordingly, by reason of demonstrated efficacy in the growth inhibition of this particular species, it is expected that these compositions will exhibit similar growth inhibition attributes when other aerobic or anaerobic bacterial species are encountered. It is also expected that these compositions will exhibit similar growth inhibition when fungi and algae species are encountered.

In accordance with the present invention, the combined glutaraldehyde and DBNPA treatment may be added to the desired aqueous system in need of biocidal treatment, in an amount of from about 0.1 to about 200 parts of the combined treatment to one million parts (by weight) of the aqueous medium. Preferably about 5 to about 50 parts of the combined treatment per one million parts (by weight) of the aqueous medium is added.

The combined treatment is added, for example, to cooling water systems, paper and pulp mill systems, waste water systems, pools, ponds, lagoons, lakes, etc., to control the formation of bacterial microorganisms which may be contained by, or which may become entrained in, the system to be treated. It has been found that the compositions and methods of utilization of the treatment are efficacious in controlling the facultative bacterium, *Klebsiella pneumoniae*, which may populate these systems. It is thought that the combined treatment composition and method of the present invention will also be efficacious in inhibiting and controlling all types of aerobic and anaerobic bacteria.

Surprisingly, it has been found that when the ingredients are mixed in certain instances, the resulting mixtures possess a higher degree of bactericidal activity than that of the individual ingredients comprising the mixture. Because of the enhanced activity of the mixture, the total quantity of the biocidal treatment may be reduced. In addition, the high degree of bactericidal effectiveness which is provided by each of the ingredients may be exploited without use of higher concentrations of each.

The following experimental data were developed. It is to be remembered that the following examples are to be regarded solely as being illustrative and not as restricting the scope of the invention.

DESCRIPTION OF THE PREFERRED EMBODIMENT

Glutaraldehyde and DBNPA were added in varying ratios over a wide range of concentrations to a liquid nutrient medium which was subsequently inoculated with a standard volume of a suspension of the facultative bacterium *Klebsiella pneumoniae*. Growth was measured by turbidity at 590 nm in a microplate spectrophotometer. The effect of the biocide chemicals, alone and in combination, is to reduce the growth (turbidity) of the bacterial cells as compared to controls not treated with the chemicals. Additions of the biocides, alone and in varying combinations and concentrations, were made according to the accepted "checkerboard" technique described by M. T. Kelly and J. Matsen, *Antimicrobial Agents and Chemotherapy*. 9:440 (1976). Growth was measured after overnight incubation at 30° C. Each unique sample concentration was tested in triplicate. The percent reduction of each treated sample was calculated from the relationship:

$$\frac{(\text{Turbidity 590 nm})_{control} - (\text{Turbidity 590 nm})_{treated}}{(\text{Turbidity 590 nm})_{control}} \times 100 = \% \text{ reduction}$$

Plotting the % reduction of turbidity against the concentration of each biocide acting alone results in a dose-response curve, from which the biocide dose necessary to achieve a given % reduction can be interpolated.

Synergism was determined by the method of calculation described by F. C. Kull, P. C. Eisman, H. D. Sylwestrowicz and R. L. Mayer, *Applied Microbiology*, 9:538 (1961) using the relationship:

$$(Q_A/Q_a)+(Q_B/Q_b)=\text{Synergism Index (SI)}$$

wherein:
  $Q_a$=quantity of compound A, acting alone, producing an end point
  $Q_b$=quantity of compound B, acting alone, producing an end point
  $Q_A$=quantity of compound A, in mixture, producing an end point
  $Q_B$=quantity of compound B, in mixture, producing an end point The end point used in the calculations is the % reduction caused by each mixture of A and B. $Q_A$ and $Q_B$ are the individual concentrations in the A/B mixture causing a given % reduction. $Q_A$ and $Q_B$ are determined by interpolation from the respective dose-response curves of A and B as those concentrations of A and B acting alone which produce the same % reduction as each specific mixture produced.

Dose-response curves for each active acting alone were determined by linear regression analysis of dose-response data. Data were fitted to a curve represented by the equation shown with each data set. After linearizing the data, the contributions of each biocide component in the biocide mixtures to the inhibition of turbidity were determined by a linear regression method with the dose-response curve of the respective biocide. If, for example, quantities of $Q_A$ and $Q_B$ are sufficient to give a 50% reduction in turbidity, $Q_a$ and $Q_b$ are those quantities of A and B acting alone respectively, found to give 50% reduction in turbidity. A synergism index (SI) is calculated for each combination of A and B.

Where the SI is less than 1, synergism exists. Where the SI=1, additivity exists. Where SI is greater than 1, antagonism exists.

The data in the following tables come from treating *Klebsiella pneumoniae*, a common nuisance bacterial type found in industrial cooling waters and in pulping and paper making systems, with varying ratios and concentrations of glutaraldehyde and DBNPA. Shown for each combination is the % reduction of turbidity (%I), the calculated SI, and the weight ratio of glutaraldehyde and DBNPA.

TABLE I

Glutaraldehyde vs. DBNPA (Standard Linear Regression Method)

| ppm Glutaraldehyde | ppm DBNPA | Ratio Glutaraldehyde:DBNPA | % I | SI |
|---|---|---|---|---|
| 9.4 | 0 | 100:0 | 0 | — |
| 18.8 | 0 | 100:0 | 0 | — |
| 37.5 | 0 | 100:0 | 6 | — |
| 75 | 0 | 100:0 | 22 | — |
| 150 | 0 | 100:0 | 53 | — |
| 300 | 0 | 100:0 | 100 | — |
| 0 | 3.2 | 0:100 | 60 | — |
| 0 | 6.3 | 0:100 | 62 | — |
| 0 | 12.5 | 0:100 | 65 | — |
| 0 | 25 | 0:100 | 72 | — |
| 0 | 50 | 0:100 | 86 | — |
| 0 | 100 | 0:100 | 100 | — |
| 9.4 | 3.2 | 3:1 | 4 | 0.77* |
| 18.8 | 3.2 | 6:1 | 5 | 2.06 |
| 37.5 | 3.2 | 12:1 | 13 | 0.66* |
| 75 | 3.2 | 24:1 | 30 | 0.73* |
| 150 | 3.2 | 48:1 | 96 | 0.64* |
| 300 | 3.2 | 96:1 | 100 | 1.17 |
| 9.4 | 6.3 | 1.5:1 | 8 | 0.16* |
| 18.8 | 6.3 | 3:1 | 5 | 0.48* |
| 37.5 | 6.3 | 6:1 | 7 | 0.89* |
| 75 | 6.3 | 12:1 | 16 | 1.15 |
| 150 | 6.3 | 24:1 | 100 | 0.65* |
| 300 | 6.3 | 48:1 | 99 | 1.23 |
| 9.4 | 12.5 | 1:1.3 | 3 | 0.19* |
| 18.8 | 12.5 | 1.5:1 | 8 | 0.32* |
| 37.5 | 12.5 | 3:1 | 13 | 0.53* |
| 75 | 12.5 | 6:1 | 34 | 0.44* |
| 150 | 12.5 | 12:1 | 100 | 0.74* |
| 300 | 12.5 | 24:1 | 100 | 1.30 |
| 9.4 | 25 | 1:2.7 | 94 | 0.43* |
| 18.8 | 25 | 1:1.3 | 32 | −0.34* |
| 37.5 | 25 | 1.5:1 | 31 | −0.14* |
| 75 | 25 | 3:1 | 59 | 14.95 |
| 150 | 25 | 6:1 | 100 | 0.90* |
| 300 | 25 | 12:1 | 100 | 1.48 |
| 9.4 | 50 | 1:5.3 | 97 | 0.77* |
| 18.8 | 50 | 1:2.7 | 100 | 0.74* |
| 37.5 | 50 | 1:1.3 | 99 | 0.83* |
| 75 | 50 | 1.5:1 | 88 | 1.27 |
| 150 | 50 | 3:1 | 99 | 1.25 |
| 300 | 50 | 6:1 | 99 | 1.82 |
| 9.4 | 100 | 1:10.7 | 99 | 1.41 |
| 18.8 | 100 | 1:5.3 | 100 | 1.42 |
| 37.5 | 100 | 1:2.7 | 100 | 1.48 |
| 75 | 100 | 1:1.3 | 100 | 1.63 |
| 150 | 100 | 1.5:1 | 100 | 1.92 |
| 300 | 100 | 3:1 | 100 | 2.49 |

TABLE II

Glutaraldehyde vs. DBNPA (Standard Linear Regression Method)

| ppm Glutaraldehyde | ppm DBNPA | Ratio Glutaraldehyde:DBNPA | % I | SI |
|---|---|---|---|---|
| 9.4 | 0 | 100:0 | 2 | — |
| 18.8 | 0 | 100:0 | 6 | — |
| 37.5 | 0 | 100:0 | 13 | — |
| 75 | 0 | 100:0 | 28 | — |
| 150 | 0 | 100:0 | 58 | — |
| 300 | 0 | 100:0 | 100 | — |
| 0 | 3.2 | 0:100 | 84 | — |
| 0 | 6.3 | 0:100 | 85 | — |
| 0 | 12.5 | 0:100 | 87 | — |
| 0 | 25 | 0:100 | 89 | — |
| 0 | 50 | 0:100 | 95 | — |
| 0 | 100 | 0:100 | 100 | — |
| 9.4 | 3.2 | 3:1 | 9 | 0.35* |
| 18.8 | 3.2 | 6:1 | 15 | 0.43* |
| 37.5 | 3.2 | 12:1 | 6 | 1.88 |
| 75 | 3.2 | 24:1 | 48 | 0.58* |
| 150 | 3.2 | 48:1 | 99 | 0.64* |
| 300 | 3.2 | 96:1 | 100 | 1.21 |
| 9.4 | 6.3 | 1.5:1 | 18 | 0.17* |
| 18.8 | 6.3 | 3:1 | 23 | 0.28* |
| 37.5 | 6.3 | 6:1 | 27 | 0.49* |
| 75 | 6.3 | 12:1 | 35 | 0.78* |
| 150 | 6.3 | 24:1 | 99 | 0.67* |
| 300 | 6.3 | 48:1 | 100 | 1.26 |
| 9.4 | 12.5 | 1:1.3 | 61 | −0.06* |
| 18.8 | 12.5 | 1.5:1 | 38 | 0.13* |
| 37.5 | 12.5 | 3:1 | 35 | 0.35* |
| 75 | 12.5 | 6:1 | 68 | 0.25* |
| 150 | 12.5 | 12:1 | 100 | 0.76* |
| 300 | 12.5 | 24:1 | 90 | 1.79 |
| 9.4 | 25 | 1:2.7 | 96 | 0.49* |
| 18.8 | 25 | 1:1.3 | 59 | −0.11* |
| 37.5 | 25 | 1.5:1 | 33 | 0.32* |
| 75 | 25 | 3:1 | 68 | 0.06* |
| 150 | 25 | 6:1 | 100 | 0.93* |
| 300 | 25 | 12:1 | 99 | 1.53 |
| 9.4 | 50 | 1:5.3 | 100 | 0.74* |
| 18.8 | 50 | 1:2.7 | 100 | 0.78* |
| 37.5 | 50 | 1:1.3 | 100 | 0.86* |
| 75 | 50 | 1.5:1 | 100 | 1.00 |
| 150 | 50 | 3:1 | 100 | 1.29 |
| 300 | 50 | 6:1 | 100 | 1.89 |
| 9.4 | 100 | 1:10.7 | 100 | 1.45 |
| 18.8 | 100 | 1:5.3 | 100 | 1.47 |
| 37.5 | 100 | 1:2.7 | 99 | 1.65 |
| 75 | 100 | 1:1.3 | 99 | 1.73 |
| 150 | 100 | 1.5:1 | 99 | 2.11 |
| 300 | 100 | 3:1 | 100 | 2.59 |

In Tables I and II, differences seen between the replicates are due to normal experimental variance. In the SI column, all numbers less than 1 (marked by an asterisk) indicate synergistic combinations in accordance with the Kull et al. method supra.

In accordance with Tables I–II supra., unexpected results occurred more frequently within the product ratios of glutaraldehyde to DBNPA of from about 24:1 to 1:5.3. Since the glutaraldehyde product contains about 50% active biocidal component, and the DBNPA product contains about 20% active biocidal component, when based on the active biocidal component, unexpected results appear more frequently within the range of active component of glutaraldehyde:DBNPA of about 60:1 to 1:2.1. Preferably the range of active component of glutaraldehyde:DBNPA is about 30:1 to about 1:1.1 and more preferably 15:1 to about 1:1. At present, it is most preferred that any commercial product embodying the invention comprises a weight ratio of active component of about 2:1 glutaraldehyde:DBNPA.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A microbial inhibiting composition comprising a synergistic mixture of (a) glutaraldehyde and (b) 2,2-dibromo- 3-nitrilopropionamide wherein the weight ratio of (a):(b) is from about 60:1 to about 1:2.1.

2. The composition as recited in claim 1 wherein the weight ratio of (a):(b) is from about 30:1 to about 1:1.1.

3. The composition as recited in claim 1 wherein the weight ratio of (a):(b) is from about 15:1 to about 1:1.

4. The composition as recited in claim 1 wherein the weight ratio of (a) to (b) is about 2:1.

5. A method for controlling the growth of microbes in an aqueous system which comprises adding to said system from about 0.1 to 200 parts per weight of a composition per one million parts per weight of said aqueous system, said composition comprising a synergistic mixture of (a) glutaraldehyde and (b) 2,2-dibromo-3-nitrilopropionamide, the weight ratio of (a) to (b) being about 60:1 to about 1:2.1.

6. The method as recited in claim 5 wherein the weight ratio of (a):(b) is from about 30:1 to about 1:1.1.

7. The method as recited in claim 5 wherein the weight ratio of (a):(b) is from about 15:1 to about 1:1.

8. The method as recited in claim 5 wherein the weight ratio of (a):(b) is about 2:1.

9. The method as recited in claim 5 wherein said composition is added to said system in an amount of from about 5 to 50 parts per million of said aqueous system.

10. The method as recited in claim 5 wherein said microbes comprise bacteria, fungi or algae.

11. The method as recited in claim 5 wherein said microbes comprise capsulated, facultative bacteria.

12. The method as recited in claim 11 wherein said capsulated, facultative bacteria comprise *Klebsiella pneumoniae*.

13. The method as recited in claim 5 wherein said aqueous system comprises a cooling water system.

14. The method as recited in claim 5 wherein said aqueous system comprises a pulping and papermaking system.

15. The method as recited in claim 5 wherein said aqueous system comprises a secondary/tertiary oil operation.

16. The method as recited in claim 5 wherein said aqueous system comprises an air washer system.

\* \* \* \* \*